United States Patent [19]

Satoh

[11] Patent Number: 5,120,758
[45] Date of Patent: Jun. 9, 1992

[54] CERTAIN BENZODIOXOLE, BENZODIOXANE AND BENZODIOXEPIN DERIVATIVES USEFUL AS 5-LIPOXYGENASE INHIBITORS

[75] Inventor: Yoshitaka Satoh, Scotch Plains, N.J.

[73] Assignee: Ciba-Geigy Corporation, Ardsley, N.Y.

[21] Appl. No.: 652,851

[22] Filed: Jul. 8, 1991

[51] Int. Cl.$^5$ .................. A61K 31/335; C07D 319/20
[52] U.S. Cl. .................... 514/452; 549/366; 549/60; 546/270; 546/256; 546/171; 546/162; 514/444; 514/333; 514/314; 514/313; 514/312
[58] Field of Search .............. 549/366, 60; 546/162, 546/171, 256, 270; 514/452, 444, 333, 312, 313, 314

[56] References Cited

U.S. PATENT DOCUMENTS

| | | | |
|---|---|---|---|
| 3,907,793 | 9/1975 | Wasson et al. | 260/247.7 |
| 4,305,955 | 12/1981 | Belletire | 424/275 |
| 4,486,428 | 12/1984 | Eggier et al. | 424/248.4 |
| 4,738,986 | 4/1988 | Kneen et al. | 514/575 |
| 4,792,560 | 12/1988 | Huang | 514/311 |
| 4,801,605 | 1/1989 | Hutchison | 514/432 |
| 4,820,828 | 4/1989 | Demers et al. | 549/362 |
| 4,873,259 | 10/1989 | Summers, Jr. et al. | 514/443 |

FOREIGN PATENT DOCUMENTS

| | | |
|---|---|---|
| 613210 | of 1962 | Belgium . |
| 292699 | 11/1988 | European Pat. Off. . |
| 313295 | 4/1989 | European Pat. Off. . |
| 313296 | 4/1989 | European Pat. Off. . |
| 408760 | 1/1991 | European Pat. Off. . |

OTHER PUBLICATIONS

Eur. J. Med. Chem. 22, 539 (1987).
Indian J. Chemistry 21B, 344(1982).
Eur. J. Med. Chem. Chim. Ther. 1982, 577-581.
J. Chem. Soc. Perkins Trans. II, 1247 (1988).
J. Chem. Soc. Perkins Trans. I, 197(1983).
J. Chem. Soc. Perkins Trans. I, 883 (1985).

Primary Examiner—Nicky Chan
Attorney, Agent, or Firm—Norbert Gruenfeld

[57] ABSTRACT

The invention relates to the compounds of the formula

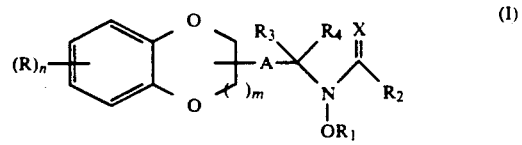

wherein each R independently represents hydrogen, lower alkyl, halogen, trifluoromethyl, lower alkoxy, carbocyclic or heterocyclic aryl, carbocyclic or heterocyclic aryloxy, carbocyclic or heterocyclic aryl-lower alkyloxy, carbocyclic or heterocyclic aryl-lower alkyl, $C_3$–$C_7$-cycloalkyl-lower alkyloxy, or $C_3$–$C_7$-cycloalkyloxy; n represents 1, 2, 3 or 4; m represents 0, 1 or 2; A represents a direct bond or lower alkylene; X represents oxygen or sulfur; $R_1$ represents hydrogen, acyl, lower alkoxycarbonyl, aminocarbonyl, mono- or di-lower alkylaminocarbonyl, lower alkenylaminocarbonyl, lower alkynylaminocarbonyl, carbocyclic or heterocyclic aryl-lower alkylaminocarbonyl, carbocyclic or heterocyclic arylaminocarbonyl, $C_3$–$C_7$-cycloalkylaminocarbonyl or $C_3$–$C_7$-cycloalkyl-lower alkylaminocarbonyl; $R_2$ represents lower alkyl, lower alkoxycarbonyl-lower alkyl, $C_3$–$C_7$-cycloalkyl, carbocyclic or heterocyclic aryl, carbocyclic or heterocyclic aryl-lower alkyl, $C_3$–$C_7$-cycloalkyl-lower alkyl, amino, mono- or di-lower alkylamino, lower alkenylamino, lower alkynylamino, carbocyclic or heterocyclic aryl-lower alkylamino, carbocyclic or heterocyclic arylamino, $C_3$–$C_7$-cycloalkylamino, $C_3$–$C_7$-cycloalkyl-lower alkylamino, lower alkoxycarbonyl-lower alkylamino or lower alkoxy; $R_3$ and $R_4$ independently represent hydrogen or lower alkyl; and pharmaceutically acceptable salts thereof; which are useful as 5-lipoxygenase inhibitors.

18 Claims, No Drawings

CERTAIN BENZODIOXOLE, BENZODIOXANE AND BENZODIOXEPIN DERIVATIVES USEFUL AS 5-LIPOXYGENASE INHIBITORS

SUMMARY OF THE INVENTION

The invention relates to the benzodioxole, benzodioxane and benzodioxepin derivatives as defined herein which are particularly useful as selective lipoxygenase inhibitors, methods for preparation thereof, pharmaceutical compositions comprising said compounds, and a method of inhibiting lipoxygenase, in particular 5-lipoxygenase, and of treating diseases in mammals which are responsive to lipoxygenase inhibition, using said compounds or pharmaceutical compositions comprising said compounds of the invention.

The compounds of the invention are particularly useful for the prevention and treatment of various inflammatory and allergic conditions, e.g. bronchial allergies and inflammatory disorders such as asthma, allergic rhinitis (hay fever), ocular allergies and inflammation, inflammatory bowel disease (including Crohn's disease, ulcerative colitis), and dermatological allergies and inflammation such as eczema and psoriasis; also for the treatment of rheumatic disorders such as rheumatoid arthritis, osteoarthritis and gouty arthritis; also for the treatment of ischemic conditions such as myocardial infarction and cerebral ischemia; also for the treatment of multiple sclerosis; for the treatment of endotoxin shock; for the treatment of renal disorders, such as primary nephrotic syndrome and cyclosporine-induced renal toxicity; in the treatment of certain carcinomas, e.g. to inhibit tumor metastasis; also to inhibit gastrointestinal side effects of non-steroidal antiinflammatory drugs.

DETAILED DESCRIPTION OF THE INVENTION

More particularly the invention relates to the compounds of formula I

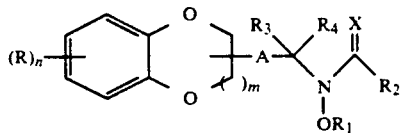

wherein each R independently represents hydrogen, lower alkyl, halogen, trifluoromethyl, lower alkoxy, carbocyclic or heterocyclic aryl, carbocyclic or heterocyclic aryloxy, carbocyclic or heterocyclic aryl-lower alkyloxy, carbocyclic or heterocyclic aryl-lower alkyl, $C_3$-$C_7$-cycloalkyl-lower alkyloxy, or $C_3$-$C_7$-cycloalkyloxy; n represents 1, 2, 3 or 4; m represents 0, 1 or 2; A represents a direct bond or lower alkylene; X represents oxygen or sulfur; $R_1$ represents hydrogen, acyl, lower alkoxycarbonyl, aminocarbonyl, mono- or di-lower alkylaminocarbonyl, lower alkenylaminocarbonyl, lower alkynylaminocarbonyl, carbocyclic or heterocyclic aryl-lower alkylaminocarbonyl, carbocyclic or heterocyclic arylaminocarbonyl, $C_3$-$C_7$-cycloalkylaminocarbonyl or $C_3$-$C_7$-cycloalkyl-lower alkylaminocarbonyl; $R_2$ represents lower alkyl, lower alkoxycarbonyl-lower alkyl, $C_3$-$C_7$-cycloalkyl, carbocyclic or heterocyclic aryl, carbocyclic or heterocyclic aryl-lower alkyl, $C_3$-$C_7$-cycloalkyl-lower alkyl, amino, mono- or di-lower alkylamino, lower alkenylamino, lower alkynylamino, carbocyclic or heterocyclic aryl-lower alkylamino, carbocyclic or heterocyclic arylamino, $C_3$-$C_7$-cycloalkylamino, $C_3$-$C_7$-cycloalkyl-lower alkylamino, lower alkoxycarbonyl-lower alkylamino or lower alkoxy; $R_3$ and $R_4$ independently represent hydrogen or lower alkyl; and pharmaceutically acceptable salts thereof.

Preferred are the said compounds of formula I wherein A represents a direct bond; X represents oxygen; and $R_1$ and $R_2$ have meaning as previously defined. Preferably $R_1$ represents hydrogen and $R_2$ represents amino or substituted amino as previously defined.

Embodiments of the invention relate to benzodioxole derivatives (wherein m represents 0), 1,4-benzodioxane derivatives (wherein m represents 1) and 1,5-benzodioxepin derivatives (wherein m represents 2).

Further embodiments relate to those wherein X represents oxygen and those wherein X represents sulfur.

The substituents represented by $(R)_n$ as defined above may be located at any of the available positions on the benzo portion of the ring system. The grouping A-Z may be located at any of the available saturated ring carbons, preferably at the position adjacent to an oxygen atom in the ring.

A preferred embodiment of the invention relates to the compounds of formula II

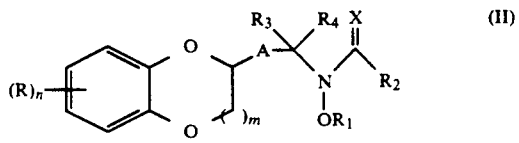

wherein R, $R_1$-$R_4$, n, m, A and X have meaning as defined above; and pharmaceutically acceptable salts thereof. Advantageously A represents a direct bond; $R_3$ and $R_4$ represent hydrogen and n represents 1 or 2.

Preferred are the compounds of formula II wherein m and n independently represent 1 or 2; X represents oxygen; A represents a direct bond; R represents hydrogen, lower alkoxy, halogen, lower alkyl, carbocyclic or heterocyclic aryl-lower alkyloxy or carbocyclic or heterocyclic aryloxy; $R_1$ represents hydrogen or acyl; $R_2$ represents lower alkyl, amino, mono- or di-lower alkylamino, or mono-carbocyclic arylamino; $R_3$ and $R_4$ independently represent hydrogen or lower alkyl; and pharmaceutically acceptable salts thereof.

Further preferred are the compounds of formula II wherein m and n represent 1; X represents oxygen; A represents a direct bond; R represents hydrogen, lower alkoxy, lower alkyl, carbocyclic aryl-lower alkyloxy or carbocyclic aryloxy; $R_1$ represents hydrogen; $R_2$ represents lower alkyl, amino, mono- or di-lower alkylamino, or mono-carbocyclic arylamino; $R_3$ represents hydrogen or lower alkyl; $R_4$ represents hydrogen; and pharmaceutically acceptable salts thereof.

Also preferred are the hereinabove compounds of formula II wherein $R_1$ represents lower alkanoyl, aminocarbonyl, mono- or di-lower alkylaminocarbonyl, or carbocyclic arylaminocarbonyl; $R_2$ represents lower alkyl, amino, mono- or di-lower alkylamino, or mono-carbocyclic arylamino; and m, n, X, A, R, $R_3$ and $R_4$ have meaning as defined above; and pharmaceutically acceptable salts thereof.

Particularly preferred compounds are those of formula III

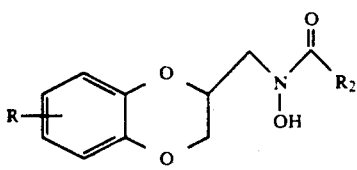

(III)

wherein R represents hydrogen, lower alkyl, carbocyclic aryl, carbocyclic aryl-lower alkyl, lower alkoxy, carbocyclic aryl-lower alkyloxy or carbocyclic aryloxy; and $R_2$ represents mono-lower alkylamino, di-lower alkylamino or amino; and pharmaceutically acceptable salts thereof.

A further aspect of the hereinabove cited compounds are the compounds of formula IV

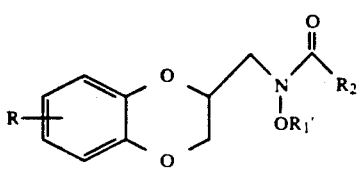

(IV)

wherein R represents hydrogen, lower alkyl, lower alkoxy, carbocyclic aryl-lower alkyloxy, or carbocyclic aryloxy; $R_1'$ represents lower alkanoyl, aminocarbonyl, or mono- or di-lower alkylaminocarbonyl; $R_2$ represents lower alkyl, amino, or mono- or di-lower alkylamino; and pharmaceutically acceptable salts thereof.

In the above compounds the substituent R is preferably attached at the 6 or 7 position of the benzodioxane ring, and advantageously represents carbocyclic aryloxy.

The general definitions used herein have the following meaning within the scope of the present invention.

The term "lower" referred to above and hereinafter in connection with organic radicals or compounds respectively defines such as branched or unbranched with up to and including 7, preferably up to and including 4 and advantageously one or two carbon atoms.

A lower alkyl group preferably contains 1–4 carbon atoms, advantageously 1–3 carbon atoms, and represents for example ethyl, propyl, butyl or most advantageously methyl.

A lower alkenyl group, as in lower alkenylamino, is preferably bonded on a saturated carbon. Such group preferably has 3–7, advantageously 3 or 4 carbon atoms and is e.g. allyl.

A lower alkynyl group, as in lower alkynylamino, is preferably bonded on a saturated carbon. Such group preferably has 3–7, advantageously 3 or 4 carbon atoms and is e.g. propargyl.

A lower alkoxy (or alkyloxy) group preferably contains 1–4 carbon atoms, advantageously 1–3 carbon atoms, and represents for example methoxy, ethoxy, propoxy or isopropoxy.

Halogen preferably represents chloro or fluoro but may also be bromo or iodo.

Aryl represents carbocyclic or heterocyclic aryl.

Carbocyclic aryl represents for example phenyl or phenyl mono- or di-substituted by one or two radicals selected from lower alkyl, lower alkoxy, halogen, cyano and trifluoromethyl; or 1- or 2-naphthyl. Preferred it is phenyl or phenyl monosubstituted by halogen or trifluoromethyl.

Heterocyclic aryl represents for example pyridyl, quinolyl or thienyl, or any said radical substituted by lower alkyl or halogen. Pyridyl represents 2-, 3- or 4-pyridyl, advantageously 2- or 3-pyridyl. Thienyl represents 2- or 3-thienyl, advantageously 2-thienyl. Quinolyl represents preferably 2-, 3- or 4-quinolyl, advantageously 2-quinolyl.

Carbocyclic aryl-lower alkyl represents preferably straight chain or branched aryl-$C_1$–$C_4$-alkyl in which carbocyclic aryl has meaning as defined above, e.g. benzyl or phenyl-(ethyl, propyl or butyl), each unsubstituted or substituted on phenyl ring as defined under carbocyclic aryl above.

Heterocyclic aryl-lower alkyl represents preferably straight chain or branched heterocyclic aryl-$C_1$–$C_4$-alkyl in which heterocyclic aryl has meaning as defined above, e.g. 2-, 3- or 4-pyridylmethyl or (2-, 3- or 4-pyridyl)-(ethyl, propyl or butyl); or 2- or 3-thienylmethyl or (2- or 3-thienyl)-(ethyl, propyl or butyl); and the like.

Similarly the terms carbocyclic aryl, heterocyclic aryl, lower alkyl, lower alkenyl, lower alkynyl have meaning as defined above in any groups in which such appear, e.g. aryloxy, aryl-lower alkyloxy and the like.

Acyl is preferably lower alkanoyl or aroyl.

Lower alkanoyl represents preferably $C_2$–$C_4$-alkanoyl such as acetyl or propionyl.

Aroyl represents preferably benzoyl or benzoyl mono- or di-substituted by one or two radicals selected from lower alkyl, lower alkoxy, halogen, cyano and trifluoromethyl; or 1- or 2-naphthoyl.

Lower alkoxycarbonyl represents preferably $C_1$–$C_4$-alkoxycarbonyl, e.g. ethoxy.

Substituted amino represents preferably mono- or di-lower alkylamino or mono-carbocyclic arylamino.

$C_3$–$C_7$-Cycloalkyl represents cyclopropyl, cyclobutyl, cyclopentyl, cyclohexyl or cycloheptyl, preferably cyclohexyl or cyclopentyl.

Lower alkylene represents either straight chain or branched $C_1$–$C_7$-alkylene and represents preferably a methylene, ethylene, propylene or butylene chain, or said methylene, ethylene, propylene or butylene chain mono-substituted by $C_1$–$C_3$-alkyl or disubstituted on the same or different carbon atoms by $C_1$–$C_3$-alkyl (advantageously methyl), the total number of carbon atoms being up to and including 7.

Pharmaceutically acceptable salts of the acidic compounds of the invention (provided that $R_1$ represents hydrogen) are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methylammonium salts.

Similarly acid addition salts, such as of mineral acids, e.g. hydrochloric acid, are also possible provided a basic group, such as pyridyl, constitutes part of the structure.

The compounds of the invention exhibit valuable pharmacological properties in mammals, and are particularly useful as selective 5-lipoxygenase inhibitors for the treatment of e.g. inflammatory, allergic and ischemic conditions.

The above-cited properties are demonstrable in in vitro and in vivo tests, using advantageously mammals, e.g. rats, guinea pigs, dogs, rabbits or isolated organs, tissues, and enzyme preparations thereof, as well as cells and fluids isolated from mammalian, including human, blood. Said compounds can be applied in vitro in the form of solutions, e.g. preferably aqueous solutions, and in vivo either enterally or parenterally, advantageously orally, e.g. as a suspension or in aqueous solution. The dosage in vitro may range between about $10^{-5}$ molar and $10^{-8}$ molar concentrations. The dosage in vivo may range, depending on the route of administration, between about 0.01 and 30 mg/kg.

5-HETE and various leukotriene products are formed from arachidonic acid by means of the enzyme 5-lipoxygenase. Leukotrienes (LTs) $B_4$, $C_4$, $D_4$ and $E_4$ are a group of mediators with potent leukocyte-chemoattractant, smooth muscle-constricting and vascular permeability-enhancing properties. $LTB_4$ is among the most potent leukocyte chemotactic agents known. $LTC_4$, $LTD_4$ and $LTE_4$ are components of the "slow-reacting substance of anaphylaxis" (SRS-A) and are potent inducers of broncho-constriction that are released during an antigen challenge in lungs. Leukotrienes have been implicated in the pathogenesis of a variety of vascular and pulmonary disorders involving leukocyte and smooth muscle activation. Since these products are derived from the biotransformation of arachidonic acid (AA) through the 5-lipoxygenase pathway, inhibition of 5-lipoxygenase will suppress biosynthesis of leukotrienes in leukocytes and various organ systems.

Beneficial effects are evaluated in pharmacological tests generally known in the art, e.g. as illustrated herein.

5-Lipoxygenase inhibition is determined e.g. by measuring the percent inhibition of the synthesis of 5-HETE [(5S)-5-hydroxy-6,8,11,14-eicosa-tetraenoic acid] and leukotriene $B_4$ ($LTB_4$, 5,12-dihydroxy-6,8,10,14-eicosatetraenoic acid) in A-23187-stimulated guinea pig polymorphonuclear leukocytes, essentially according to radiometric thin-layer chromatographic assays described by Walker and Dawson (J. Pharm. Pharmacol. 31: 778, 1979) and Jakschik and Lee (Nature 287: 51, 1980) to measure the formation of 5-HETE and $LTB_4$-like products from $^{14}$C-arachidonic acid. $IC_{50}$ values are determined graphically as the concentration of test compound at which the synthesis of 5-HETE and $LTB_4$-like products is reduced to 50% of their respective control values.

The inhibition of $LTB_4$ formation can also be determined in vitro in whole blood from dogs. One ml samples of blood are preincubated at 37° C. for 5 minutes with the desired concentration of test compound added as a solution in 10 microliters of dimethylsulfoxide. $LTB_4$ synthesis is then stimulated by the addition of A-23187 and N-formyl-met-leu-phe (f-MLP). The amount of $LTB_4$ is measured in the separated plasma fraction by radioimmunoassay. $IC_{50}$ values are determined graphically as the concentration of test compound causing 50% inhibition of $LTB_4$ formation seen in control whole blood.

Furthermore, the inhibition of 5-lipoxygenase is determined after oral or i.v. administration to rats or dogs by measuring ex vivo in whole blood the decrease of A-23187-stimulated $LTB_4$ formation as compared to non-treated control animals.

Antiiflammatory activity can be demonstrated by measuring the inhibition of the edema and inhibition of the influx of polymorphonuclear (PMN's) and mononuclear leukocytes (monocytes and macrophages) after oral administration in the rat model in which pleurisy is first induced by injecting carrageenin into the pleural cavity, e.g. according to A. P. Almeida et al., J. Pharmacol. Exp. Therap. 214, 74 (1980), in particular during the late phase of the corrageenin-induced pleurisy.

Bronchial effects such as anti-asthmatic activity, can be demonstrated in the antigen-induced guinea pig bronchoconstriction test, e.g. as described by Anderson et al, Br. J. Pharmacol. 1983, 78, 67–74.

The trinitrobenzenesulfonic acid-induced chronic colitis test in the rat, e.g. as described by Wallace et al, Gastroenterology 1989, 96, 29–36, can be used to evaluate compounds for effects indicative of utility in inflammatory bowel diseases.

The arachidonic acid-induced mouse ear edema test, e.g. as described by Young et al, J. Invest. Dermatol. 1984, 82, 367–371 can be used to evaluate compounds for effects indicative of utility in dermatological disorders such as psoriasis.

Illustrative of the invention, the compound of example 1(c), 2-(N-amino-carbonyl-N-hydroxy)aminomethyl-7-(4-fluorophenoxy))-1,4-benzodioxane, inhibits the formation of 5-HETE [(5S)-5-hydroxy-6,8,11,14-eicosatetraenoic acid] and leukotriene $B_4$ ($LTB_4$, 5,12-dihydroxy-6,8,10,14-eicosatetraenoic acid) in A-23187-stimulated guinea pig polymorphonuclear leukocytes, at an $IC_{50}$ of about 0.10 and 0.12 micromolar, respectively. Said compound also causes significant inhibition of $LTB_4$ formation as determined ex vivo when administered at a dose of about 1.0 mg/kg p.o. to the dog.

The compounds of the invention are thus useful, particularly for the treatment and amelioration of diseases and conditions in mammals, including man, in which lipoxygenase activity or the accumulation of leukocytes (e.g. neutrophils) is involved, particularly allergic and inflammatory disorders, e.g. pulmonary allergies and inflammatory disorders (such as asthma), dermatological allergies and inflammatory disorders (such as psoriasis), also arthritic disorders (such as rheumatoid arthritis and osteoarthritis), ocular allergies and inflammatory disorders, gastrointestinal inflammatory disorders (such as inflammatory bowel diseases), as well as ischemic conditions (such as in myocardial infraction).

The compounds of formula I of the invention, depending on the structural type involved, can be prepared by the following synthetic processes:

Process (a) —by condensing a hydroxylamine of formula V

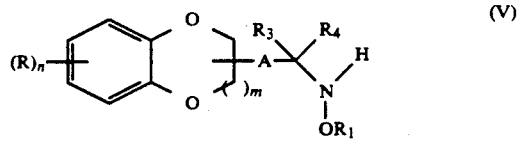

wherein R, $R_1$, $R_3$, $R_4$, A, m and n have meaning as defined hereinabove, with a compound of formula VI $R_2'$—COOH (VI)

in the presence of a condensing agent, or a reactive functional derivative thereof, wherein $R_2'$ represents lower alkyl, lower alkoxycarbonyl-lower alkyl, $C_3$-$C_7$-cycloalkyl, carbocyclic or heterocyclic aryl, carbocyclic or heterocyclic aryl-lower alkyl, $C_3$-$C_7$-cycloalkyl-lower alkyl, lower alkoxy or di-lower alkylamino, to obtain said compounds of formula I wherein X represents O and $R_2$ corresponds to $R_2'$; or process (b) —by condensing a compound of the formula V above with phosgene or thiophosgene, followed by an amine of the formula VII $$R_2''-H \qquad (VII)$$

wherein $R_2''$ represents amino, mono- or di-lower alkylamino, lower alkenylamino, lower alkynylamino, carbocyclic or heterocyclic arylamino, $C_3$-$C_7$-cycloalkylamino, carbocyclic or heterocyclic aryl-lower alkylamino, $C_3$-$C_7$-cycloalkyl-lower alkylamino, or lower alkoxycarbonyl-lower alkylamino, to obtain said compounds of formula I wherein $R_2$ corresponds to $R_2''$; or process (c) —by condensing a compound of formula V above with an isocyanate or isothiocyanate of the formula VIII $$R_5-N=C=X \qquad (VIII)$$

wherein X represents O or S, and $R_5$ represents a protecting group (such as tri-lower alkyl silyl), lower alkyl, lower alkenyl, lower alkynyl, carbocyclic or heterocyclic aryl, $C_3$-$C_7$-cycloalkyl, $C_3$-$C_7$-cycloalkyl-lower alkyl, carbocyclic or heterocyclic aryl-lower alkyl, or lower alkoxycarbonyl-lower alkyl; and if required removing the protecting group, e.g. the tri-lower alkyl silyl group when $R_5$ represents the tri-lower alkyl silyl protecting group, to obtain said compounds of formula I wherein $R_2$ corresponds to $R_5NH$ in which $R_5$ represents hydrogen and groups as defined above.

In the above cited processes, the said process is carried out while, if necessary, temporarily protecting any interfering reactive group(s), and then liberating the resulting compound of the invention; and, if required or desired, a resulting compound of the invention is converted into another compound of the invention, and/or, if desired, a resulting free compound is converted into a salt or a resulting salt is converted into a free compound or into another salt; and/or a mixture of isomers or racemates obtained is separated into the single isomers or racemates; and/or, if desired, a racemate is resolved into the optical antipodes.

In starting compounds and intermediates which are converted to the compounds of the invention in a manner described herein, functional groups present, such as amino and hydroxy groups, are optionally protected by conventional protecting groups that are common in preparative organic chemistry. Protected amino and hydroxy groups are those that can be converted under mild conditions into free amino and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, for example, in J. F. W. McOmie, "Protective Groups in Organic Chemistry", Plenum Press, London, New York, 1973, T. W. Greene, "Protective Groups in Organic Synthesis", Wiley, New York, 1984.

In the processes cited herein, reactive functional derivatives of carboxylic acids represent, for example, anhydrides especially mixed anhydrides, acid halides, acid azides, lower alkyl esters and activated esters thereof. Mixed anhydrides are preferably such from pivalic acid, or a lower alkyl (ethyl, isobutyl) hemiester of carbonic acid; acid halides are for example chlorides or bromides; activated esters are for example succinimido, phthalimido or 4-nitrophenyl esters; lower alkyl esters are for example the methyl or ethyl esters.

Also, a reactive esterified derivative of an alcohol in any of the processes cited herein represents said alcohol esterified by a strong acid, especially a strong inorganic acid, such as a hydrohalic acid, especially hydrochloric, hydrobromic or hydroiodic acid, or sulphuric acid, or by a strong organic acid, especially a strong organic sulfonic acid, such as an aliphatic or aromatic sulfonic acid, for example methanesulfonic acid, 4-methylbenzenesulfonic acid or 4-bromobenzenesulfonic acid. A said reactive esterified derivative is especially halo, for example chloro, bromo or iodo, or aliphatically or aromatically substituted sulfonyloxy, for example methanesulfonyloxy or 4-methylbenzenesulfonyloxy (tosyloxy).

The above processes for the synthesis of compounds of the invention can be carried out according to methodology generally known in the art for the preparation of hydroxylamine derivatives.

The synthesis according to process (a) involving the condensation of carboxylic acid of formula VI or a reactive functional derivative thereof with a hydroxylamine derivative of formula V (optionally hydroxy protected with $R_1$ represents hydrogen) can be carried out in the presence of a condensing agent, e.g. diethyl phosphonocyanidate, 1,1'-carbonyldiimidazole or dicyclohexylcarbodiimide, in an inert polar solvent, such as dimethylformamide or dichloromethane.

The synthesis according to process (a) involving the condensation of a reactive functional derivative of an acid of formula VI as derived above, e.g. an acid chloride or mixed anhydride with an optionally hydroxy protected hydroxylamine derivative of formula V, or a salt thereof, in the presence of a base such as triethylamine can be carried out at a temperature ranging preferably from about $-78°$ C. to $+75°$ C., in an inert organic solvent such as dichloromethane or toluene.

In the case of acylation of the compounds of formula V wherein $R_1$ represents hydrogen, e.g. with 2 mole equivalents or excess of a functional derivative of a compound of formula VI, the N,O-bis-acylated compounds of formula I, namely those wherein $R_1$ represents $COR_2$, are obtained. The N,O-diacylated compounds of formula I, e.g. wherein $R_2$ represents lower alkyl or di-lower alkylamino and $R_1$ represents the corresponding $COR_2$ group, can be selectively O-deacylated under basic conditions, e.g., with aqueous lithium hydroxide to yield the corresponding compounds of formula I wherein $R_1$ represents hydrogen.

Processes (b) and (c) are directed to the preparation of urea derivatives, the compounds of formula I wherein $R_2$ represents amino or substituted amino, from hydroxylamines of formula V.

The preparation according to process (b) can be carried out by reacting the hydroxylamine derivative of formula V, optionally in hydroxy-protected form, with phosgene or thiophosgene in an inert solvent such as toluene followed by condensation with the appropriate amine at a temperature of about $-25°$ C. to $+150°$ C.

The preparation according to process (c) involves the condensation of a hydroxylamine of formula V or a salt thereof, optionally in hydroxy-protected form, with e.g. the isocyanate in an inert solvent such as toluene, acetonitrile or dioxane at a temperature ranging from −10° C. to reflux temperature.

In the case of reaction of compounds of formula V wherein $R_1$ represents hydrogen with 2 moles of a compound of formula VIII, compounds of formula I wherein $R_1$ represents e.g. $COR_2$ can be obtained.

Protected forms of hydroxylamines of formula V wherein $R_1$ represents hydrogen in the above processes are those within the hydroxy group is protected for example as a benzyl ether or tetrahydropyranyl ether. Removal of said protecting groups is carried out according to methods well known in the art, e.g. hydrogenolysis or acid hydrolysis, respectively.

The carboxylic acids of VI and reactive derivatives thereof are known in the art or can be prepared according to methods well-known in the art; similarly the amines of formula VII, and the isocyanates and isothiocyanates of formula VIII are known in the art or can be prepared according to methods well-known in the art.

The starting hydroxylamine derivatives of formula V may be prepared from a corresponding reactive derivative of an alcohol of formula IX

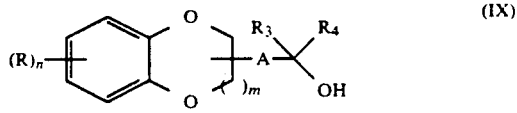

wherein R, $R_3$, $R_4$, A, m and n have meaning as defined hereinabove, such as the corresponding bromide, iodide, tosylate or mesylate derivative, by condensing such with a protected hydroxylamine derivative, e.g. N,O-bis(tert-butoxycarbonyl)hydroxylamine, followed by deprotection, e.g. with trifluoroacetic acid.

Alternatively hydroxylamines of formula V wherein at least one of $R_3$ or $R_4$ represents hydrogen can be prepared from the corresponding aldehyde or ketone by conversion to the oxime with e.g. hydroxylamine hydrochloride according to known methods, followed by reduction to the hydroxylamine with e.g. borane-pyridine complex or sodium cyanoborohydride in acidic medium.

The alcohols of formula IX and the corresponding aldehydes or ketones may be prepared e.g. from the corresponding acids of formula X

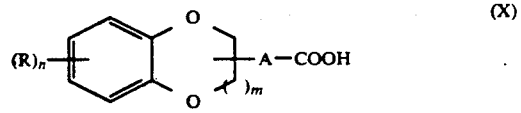

or ester derivatives thereof according to methods well-known in the art. For example, such can be reduced to the alcohol wherein $R_3$ and $R_4$ represent hydrogen using an appropriate reducing agent such as lithium aluminum hydride or borane-tetrahydrofuran complex.

The carboxylic acids of formula X or ester derivatives of thereof wherein m represents 0 can be obtained from the corresponding catechol e.g as described in U.S. Pat. No. 2,979,511 or J. Amer. Chem. Soc. 66, 312 (1944).

Carboxylic acids of formula X or ester derivatives of thereof wherein m represents 1 can be obtained from the corresponding catechol, e.g. as described in J. Org. Chem. 39, 1808, 1974.

Carboxylic acids of formula X and ester derivatives thereof wherein m represents 2 and A is located at position 2 of the benzodioxepin ring can be obtained from the corresponding catechol, e.g. by the method described in Belgium Patent 613,210.

Alcohols of formula IX wherein m represents 2 and A is located at position 3 of the benzodioxepin ring can be prepared, e.g. according to the method described in U.S. Pat. No. 3,907,793.

Furthermore, the alcohols of formula IX wherein m represents 1 and A is a direct bond can be prepared as follows by:

1) converting an appropriately substituted 2-hydroxyphenyl ketone or aldehyde to the corresponding 2-(2,3-oxopropyloxy)phenyl carboxaldehyde or ketone by treating with a 2,3-oxopropyl halide or alkanesulfonate, e.g. epibromohydrin, preferably in the presence of a base, e.g. potassium or cesium carbonate, in a polar inert organic solvent such as dimethylformamide; then 2) converting the 2-(2,3-oxopropyloxy)phenyl carboxaldehyde or ketone to the corresponding appropriately substituted 2-(2,3-oxopropyloxy)phenyl alkanoate by oxidation with, e.g. m-chloroperbenzoic acid in an inert solvent such as dichloromethane; and subsequently 3) treating the 2-(2,3-oxopropyloxy)phenyl alkanoate with a base, e.g. aqueous sodium hydroxide, to obtain the corresponding substituted 2-hydroxymethyl-1,4-benzodioxane.

The alcohols of formula IX wherein m represents 1 and A is a direct bond can also be obtained by the following sequence by:

1) converting an appropriately substituted 2-hydroxyphenyl ketone or carboxaldehyde by treating with an allylic halide or alkanesulfonate, e.g. allyl bromide, preferably in the presence of a base, such as potassium carbonate, to yield the corresponding 2-(2-propenyloxy)phenyl ketone or carboxaldehyde; then 2) converting the 2-(2-propenyloxy)phenyl ketone or carboxaldehyde to the corresponding appropriately substituted 2-(2,3-oxopropoxy)phenyl alkanoate by oxidation with, e.g. m-chloroperbenzoic acid in an inert solvent such as dichloromethane; and then 3) treating the 2-(2,3-oxopropoxy)phenyl alkanoate with a base, e.g. aqueous sodium hydroxide, to obtain the corresponding substituted 2-hydroxymethyl-1,4-benzodioxane.

Alternatively the corresponding regioisomeric alcohol of formula IX wherein m represents 1 and A is a direct bond can be prepared from the same starting 2-hydroxphenyl ketone or aldehyde as follows by:

1) protecting the hydroxy function of an appropriately substituted 2-hydroxyphenyl ketone or carboxaldehyde, e.g. by treating with benzyl bromide in the presence of a base such as potassium carbonate in an inert solvent such as dimethylformamide to the corresponding 2-benzyloxyphenyl ketone or aldehyde; and then 2) oxidizing the corresponding protected 2-hydroxyphenyl ketone or carboxaldehyde e.g. 2-benzyloxyphenyl ketone or aldehyde, with a peroxide, such as m-chloroperbenzoic acid or acidic hydrogen peroxide, to afford the corresponding 2-hydroxyphenyl alkanoate protected at 2 position, e.g. 2-benzyloxyphenyl alkanoate; and subsequently 3) hydrolyzing the protected 2-hydroxyphenyl alkanoate e.g. 2-benzyloxyphenyl alkanoate, to the corresponding mono-protected catechol, e.g. 2-benzyloxyphenol, by treating with a base, e.g. aqueous sodium or lithium hydroxide; then 4) converting the appropriately substituted, protected catechol, e.g. 2-benzyloxyphenol, by treating with 2,3-oxopropyl halide or 2,3-oxopropylsulfonate, e.g. epibromohydrin, preferably in the presence of a base such as potassium or cesium carbonate in a polar solvent e.g. dimethylformamide to afford the corresponding protected ortho-(2,3-oxopropyloxy)-phenol, e.g. 2-benzyloxy-1-(2,3-oxopropyloxy)benzene; and subsequently 5) deprotecting the appropriately substituted protected ortho-(2,3-oxopropyloxy)-phenol, e.g. 1-(2,3-oxopropoxy)-2-benzyloxybenzene, by the method known in the art, e.g. by treating with hydrogen in the presence of a catalyst, e.g. palladium on charcoal, in a solvent such as ethyl acetate to afford 2-(2,3-oxopropyloxy)-phenol; and finally 6) treating the corresponding 2-(2,3-oxopropyloxy)-phenol with a base such as aqueous sodium hydroxide to afford the appropriately substituted 2-hydroxymethyl-1,4-benzodioxane.

The above-mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative examples.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes.

Advantageously those starting materials are used in said reactions that lead to the formation of those compounds indicated above as being preferred.

Compounds of the invention can also be converted into each other according to methods generally known per se. For example, compounds of formula I wherein X represents oxygen e.g. wherein $R_1$ represents acyl, can be converted to the corresponding compounds wherein X represents sulfur by reaction with e.g. Lawesson's reagent.

The invention also relates to any novel starting materials and processes for their manufacture.

Depending on the choice of starting materials and methods, the new compounds may be in the form of one of the possible isomers or mixtures thereof, for example, optical isomers (antipodes), racemates, or mixtures thereof. The aforesaid possible isomers or mixtures thereof are within the purview of this invention.

Any resulting mixtures of isomers can be separated on the basis of the physico-chemical differences of the constituents, into the pure isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound. The hydroxamic acids (wherein $R_1$ represents hydrogen) can thus be resolved into their optical antipodes e.g. by fractional crystallization of d- or l-(alpha-methylbenzylamine, cinchonidine, cinchonine, quinine, quinidine, ephedrine, dehydroabietylamine, brucine or strychnine)-salts.

Finally, acidic compounds of the invention are either obtained in the free form, or as a salt thereof.

Acidic compounds of the invention may be converted into salts with pharmaceutically acceptable bases, e.g. an aqueous alkali metal hydroxide, advantageously in the presence of an ethereal or alcoholic solvent, such as a lower alkanol. From the solutions of the latter, the salts may be precipitated with ethers, e.g. diethyl ether. Resulting salts may be converted into the free compounds by treatment with acids. These or other salts can also be used for purification of the compounds obtained.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enternal, such as oral or rectal, transdermal and parenteral administration to mammals, including man, to inhibit lipoxygenase, in particular 5-lipoxygenase, and for the treatment of disorders responsive thereto, comprising an effective amount of a pharmacologically active compound of the invention, alone or in combination, with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders e.g. magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

The pharmaceutical formulations contain an effective lipoxygenase inhibiting amount of a compound of the invention as defined above either alone, or in combination with another therapeutic agent selected from e.g. an anti-inflammatory agent with cyclooxygenase inhibiting activity, a leukotriene receptor antagonist, a thromboxane synthetase inhibitor, a thromboxane receptor antagonist, an antihistamine, a platelet activating factor (PAF) antagonist or a serotonin receptor antagonist, each at an effective therapeutic dose as reported in the art. Such therapeutic agents are well-known in the art.

Examples of antiinflammatory agents with cyclooxygenase inhibiting activity are diclofenac, naproxen, ibuprofen, and the like.

Examples of leukotriene antagonists are LY-223982, SC-41930, ICI-204219, L-660711, and the like.

Examples of thromboxane synthetase inhibitors are ozagrel (OKY-046), pirmagrel (CGS 13080), CGS 12970, CGS 15435 and the like.

Examples of thromboxane receptor antagonists are sulotroban, ICI-192605, GR-32191, SQ-30741, L-655240 and the like.

Examples of antihistaminic agents are astemizole, loratidine, terfanidine, chlorpheniramine and the like.

Examples of platelet activating factor antagonists are BN-52063, WEB-2086, CV-3988, RP-48740, L-652731 and the like.

Examples of serotonin antagonists are ketanserin, cinaserin, irindalone and the like.

In conjunction with another active ingredient, a compound of the invention may be administered either simultaneously, before or after the other active ingredient, either separately by the same or different route of administration or together in the same pharmaceutical formulation.

The invention further particularly relates to a method of inhibiting 5-lipoxygenase activity in mammals including man, and of treating diseases and conditions responsive thereto, particularly inflammatory and allergic disorders, which comprises administering to a mammal in need thereof an effective amount of a compound of the invention or of a pharmaceutical composition comprising a said compound in combination with one or more pharmaceutically acceptable carriers.

Excessive lipoxygenase activity has been implicated in various diseases and abnormal metabolic conditions including:

a) allergic conditions such as hay fever (allergic rhinitis), extrinsic asthma, skin allergies, allergic bowel diseases (incl. coeliac disease), allergic eye conditions such as allergic conjuctivitis;

b) inflammatory conditions such as inflammatory bowel diseases, irritable bowel syndrome, mucous colitis, ulcerative colitis, Crohn's disease, gastritis, esophagitis, hepatitis;

c) cardiovascular conditions such as myocardial ischemia, cerebral ischemia, atherosclerosis, angina, and renal ischemia;

d) pulmonary conditions such as intrinsic asthma, bronchitis, cystic fibrosis;

e) arthritic conditions such as rheumatoid arthritis, rheumatoid spondylitis, gouty arthritis, osteoarthritis and the like;

f) cutaneous disorders such as psoriasis, eczema and dermatitis;

g) multiple sclerosis, arteriosclerosis of various etiology and shock such as endotoxin shock, and h) tumor metastasis.

Conditions or syndromes responsive to the inhibition of lipoxygenase are those cited above, e.g. rheumatic diseases such as rheumatoid arthritis, allergic disorders, asthma and psoriasis.

The dosage of active compound administered is dependent on the species of warm-blooded animal (mammal), the body weight, age and individual condition, and on the form of administration. A unit dosage for oral administration to a mammal of about 50 to 70 kg may contain between about 20 and 250 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by standard analytical methods, e.g. microanalysis and spectroscopic characteristics (e.g. MS, IR, NMR). Abbreviations used are those conventional in the art.

EXAMPLE 1 a) 2-(N-Hydroxy)aminomethyl-1,4-benzodioxane (950 mg, 5.3 mmol) is taken up in 1,4-dioxane (20 mL) and treated with trimethylsilyl isocyanate (910 mg, 7.1 mmol). The mixture is heated at reflux for 30 minutes and cooled to room temperature. The mixture is diluted with saturated aqueous ammonium chloride, and extracted with ethyl acetate. The combined organic layer is dried over magnesium sulfate, and evaporated. The residue is crystallized from ether/hexane to give 2-(N-aminocarbonyl-N-hydroxy)aminomethyl-1,4-benzodioxane, m.p. 126° C., as a colorless solid.

The starting material is prepared as follows:

2-Hydroxymethyl-1,4-benzodioxane (17.9 g, 107 mmol) is taken up in acetonitrile (200 mL) and treated with dibromotriphenylphosphorane (50 g, 119 mmol). The mixture is stirred for 30 minutes and evaporated. The residue is taken up in a 1:1 mixture of ether/hexane, and triphenylphosphine oxide is removed by filtration. The solvent is removed by evaporation to give 2-bromomethyl-1,4-benzodioxane as a brownish solid. This material is used without further purification.

N,O-Bis-tert-butoxycarbonylhydroxylamine (14.0 g, 61 mmol) is dissolved in DMF (150 mL) and treated with sodium hydride (2.64 g, 60% in mineral oil, 66 mmol). The mixture is stirred for 30 minutes. To this is added 2-bromomethyl-1,4-dioxane (10.6 g, 46 mmol) in DMF (30 mL) and the mixture is stirred overnight at room temperature. This is diluted with ether and washed with saturated aqueous ammonium chloride solution. The organic layer is dried over magnesium sulfate and evaporated. The residue is purified by silica-gel flash chromatography (3% ethyl acetate in hexane)

to give 2-(N-tert-butoxycarbonyl-N-tert-butoxycarbonyloxy)aminomethyl-1,4-benzodioxane as a pale yellow oil.

2-(N-tert-Butoxycarbonyl-N-tert-butoxycarbonyloxy)aminomethyl-1,4-benzodioxane (2.0 g, 5.3 mmol) is taken up in 20 mL of methylene chloride and treated with trifluoroacetic acid (2.45 g, 21.5 mmol) at room temperature for 30 minutes. The solvent is evaporated and the residue is diluted with ether. The organic phase is washed twice with aqueous 1N sodium hydroxide, dried over magnesium sulfate, and evaporated to give 2-(N-hydroxy)aminomethyl-1,4-benzodioxane as a colorless solid.

b) 2-(N-Hydroxy)aminomethyl-7-phenoxy-1,4-benzodioxane (420 mg, 1.54 mmol) is dissolved in 1,4-dioxane (20 mL) and treated with trimethylsilyl isocyanate (265 mg, 2.31 mmol). The mixture is heated at reflux for 30 minutes, and cooled. The mixture is diluted with ethyl acetate and washed with saturated aqueous ammonium chloride solution. The organic layer is dried over magnesium sulfate and evaporated. The residue is crystallized from ether/hexane to give 2-(N-aminocarbonyl-N-hydroxy)aminomethyl-7-phenoxy-1,4-benzodioxane, m.p. 146° C., as a colorless solid.

The starting material is prepared as follows:

4-Phenoxyphenol (20.0 g, 107 mmol) and sodium hydroxide (3.8 g, 845 mmol) are dissolved in a water/ethanol (130 mL/26 mL) mixture and heated at 70° C. To this reaction mixture is added chloroform (24.6 g, 215 mmol) dropwise over 45 minutes, and heating is continued for 3 hours. The mixture is cooled to room temperature, and then evaporated. The aqueous phase is acidified with concentrated hydrochloric acid to pH 1-3, and extracted with ether. The organic phase is dried over magnesium sulfate and evaporated. Purification of the residue by silica-gel flash chromatography gives 2-hydroxy-5-phenoxybenzaldehyde as a yellow solid.

2-Hydroxy-5-phenoxybenzaldehyde (4.23 g, 19.8 mmol) and cesium carbonate (32.2 g, 98.8 mmol) are taken in DMF (200 mL) and treated with epibromohydrin (3.25 g, 23.7 mmol). The mixture is stirred overnight at room temperature. This is diluted with ether and washed with water and brine, dried over magnesium sulfate and evaporated. Purification by silica-gel flash chromatography (4:1 hexane/ethyl acetate) gives 2(2,3-oxopropyloxy)-5-phenoxybenzaldehyde as a colorless solid.

2-(2,3-Oxopropyloxy)-5-phenoxybenzaldehyde (4.16 g, 15.4 mmol) is dissolved in methylene chloride (100 mL) and cooled to 0° C. m-Chloroperbenzoic acid (8.0 g, 80%, 36.8 mmol) is added and the mixture is stirred for 1 hour at 0° C., and then overnight at room temperature. Ether is added and the organic phase is washed three times with saturated aqueous sodium bicarbonate solution, dried over magnesium sulfate and evaporated. Purification with silica-gel flash chromatography gives 1-formyloxy-2-(2,3-oxopropyloxy)-5-phenoxybenzene as a tan solid.

1-Formyloxy-2-(2,3-oxopropyloxy)-5-phenoxybenzene (1.77 g, 6.2 mmol) is taken up in 1,4-dioxane (30 mL) and treated with aqueous 1N sodium hydroxide (8.0 mmol). The reaction is stirred at room temperature for 2 hours. The mixture is diluted with ether and extracted with saturated aqueous sodium chloride solution, dried over magnesium sulfate and evaporated. Purification with silica-gel flash chromatography gives 2-hydroxymethyl-7-phenoxy-1,4-benzodioxane as a colorless solid.

2-Hydroxymethyl-7-phenoxy-1,4-benzodioxane (1.42 g, 5.50 mmol) and triethylamine (1.11 g, 11.0 mmol) are dissolved in methylene chloride (50 mL) and treated with methanesulfonyl chloride (0.94 g, 8.26 mmol) at 0° C. The mixture is stirred at 0° C. for 30 minutes, and diluted with ether. This is washed with aqueous sodium bicarbonate, aqueous 1N hydrochloric acid and saturated aqueous ammonium chloride, dried over magnesium sulfate and evaporated to give 2-methanesulfonyloxymethyl-7-phenoxy-1,4-benzodioxane. The crude oil is used without further purification.

2-Methanesulfonyloxymethyl-7-phenoxy-1,4-benzodioxane (1.85 g, 5.5 mmol) and sodium iodide (1.54 g, 11.0 mmol) are taken up in methyl ethyl ketone (60 mL) and heated at reflux for 3 hours. The mixture is cooled, diluted with ethyl acetate, washed with aqueous sodium bicarbonate, dried over magnesium sulfate and evaporated to give 2-iodomethyl-7-phenoxy-1,4-benzodioxane as a tan solid. This is used without further purification.

2-Iodomethyl-7-phenoxy-1,4-benzodioxane is converted to 7-phenoxy-2-(N-hydroxyaminomethyl)-1,4-benzodioxane as described in Example 1(a).

The 2-hydroxymethyl-7-phenoxy-1,4-benzodioxane intermediate can also be prepared as follows:

4-Phenoxyphenol (25.0 g, 134 mmol) is taken up in a mixture of pyridine (51 mL) and acetic anhydride (58 mL) and heated at reflux for 2 hours. The mixture is cooled and poured into 300 mL of water. The solution is made acidic with 2N hydrochloric acid and extracted three times with ether. The organic phase is washed with aqueous sodium bicarbonate solution, dried over magnesium sulfate and evaporated. Purification of the residue by silica-gel flash chromatography (4:1 hexane/ethyl acetate) gives 4-phenoxyphenyl acetate as a colorless solid.

4-Phenoxyphenyl acetate (30.2 g, 133 mmol) is treated with anhydrous aluminum chloride (26.5 g, 199 mmol) at 150° C. for 3 hours. The mixture is cooled and treated slowly with water (300 mL). Three extractions with ether are carried out and the combined organic phase is dried over magnesium sulfate and evaporated. Purification of the residue by silica-gel flash chromatography (4% ethyl acetate in hexane) gives 2-acetyl-4-phenoxyphenol as a colorless solid.

2-Acetyl-4-phenoxyphenol (4.22 g, 18.5 mmol) and cesium carbonate (15.0 g, 46.0 mmol) are taken in DMF (50 mL) and treated with allyl bromide (2.24 g, 18.5 mmol). The mixture is stirred overnight at room temperature. Ether is added and the mixture is washed with saturated aqueous ammonium chloride solution. The organic phase is dried over magnesium sulfate and evaporated to give 2-acetyl-1-allyloxy-4-phenoxybenzene as a yellow solid.

2-Acetyl-1-allyloxy-4-phenoxybenzene (1.1 g, 4.0 mmol) is dissolved in methylene chloride (20 mL) and treated with m-chloroperbenzoic acid (4.34 g, 80%, 20.0 mmol) at 0° C. The mixture is stirred at 0° C. for 1 hour, and then at room temperature overnight. The mixture is diluted with ether and washed with saturated aqueous sodium bicarbonate solution. The organic phase is dried over magnesium sulfate and evaporated. Purification of the residue by silica-gel flash chromatography (9:1 hexane/ethyl acetate) gives 2-acetoxy-1-(2,3-oxypropyloxy)-4-phenoxybenzene as a colorless solid.

2-Acetoxy-1-(2,3-oxopropyloxy)-4-phenoxybenzene (560 mg, 1.89 mmol) is dissolved in 1,4-dioxane (15 mL) and treated with aqueous 1N sodium hydroxide solution (2 mL). The mixture is stirred at room temperature for 30 minutes, and diluted with ether. The organic phase is washed with saturated aqueous sodium chloride solution, dried over magnesium sulfate and evaporated to give 2-hydroxymethyl-7-phenoxy-1,4-benzodioxane as a colorless solid.

c) Similarly prepared is 2-(N-aminocarbonyl-N-hydroxy)aminomethyl-7-(4-fluorophenoxy)-1,4-benzodioxane, m.p. 168° C., as a colorless solid.

d) 2-(N-Hydroxy)aminomethyl-6-phenoxy-1,4-benzodioxane (760 mg, 2.78 mmol) is dissolved in 1,4-dioxane (10 mL) and treated with trimethylsilyl isocyanate (480 mg, 4.18 mmol). The mixture is heated at reflux for 30 minutes and cooled. This is diluted with ethyl acetate, washed with saturated aqueous ammonium chloride solution, dried over magnesium sulfate and evaporated. The residue is dissolved in ether and washed three times with aqueous 1N sodium hydroxide. The aqueous phase is acidified with 2N hydrochloric acid and extracted with ethyl acetate. The organic layer is dried over magnesium sulfate and evaporated. Crystallization of the residue gives 2-(N-aminocarbonyl-N-hydroxy)aminomethyl-6-phenoxy-1,4-benzodioxane, m.p. 136° C.

The starting material is prepared as follows:

5-Phenoxy-2-hydroxybenzaldehyde (20 g, 94 mmol) and potassium carbonate (26.1 g, 188 mmol) are taken up in DMF (250 mL) and treated with benzyl bromide (16.1 g, 94 mmol). The mixture is stirred at room temperature overnight. The mixture is diluted with ethyl acetate and washed three times with saturated aqueous ammonium chloride, dried over magnesium sulfate and evaporated to give 2-benzyloxy-5-phenoxybenzaldehyde as a colorless solid. This is used without further purification.

2-Benzyloxy-5-phenoxybenzaldehyde (22.25 g, 73 mmol) is dissolved in methanol (200 mL) and treated with hydrogen peroxide (31% in water, 32.0 mL) and concentrated sulfuric acid (15.0 mL). The mixture is stirred overnight at room temperature and evaporated. The residue is dissolved in saturated aqueous sodium chloride solution and extracted with ether. The organic phase is dried over magnesium sulfate and evaporated. Purification of the residue by silica-gel flash chromatography gives 2-benzyloxy-5-phenoxyphenol as a colorless solid.

2-Benzyloxy-5-phenoxyphenol (16 g, 55 mmol) and cesium carbonate (26.9 g, 82.5 mmol) are taken in DMF (200 mL) and treated with epibromohydrin (7.45 g, 55 mmol). The mixture is stirred at room temperature for 2 hours, and diluted with ether. The organic phase is washed several times with saturated aqueous sodium chloride solution, dried over magnesium sulfate and evaporated. Purification of the residue by silica-gel flash chromatography gives 2-(2,3-oxopropyl)oxy-4-phenoxyphenyl benzyl ether as a colorless solid.

2-(2,3-Oxopropyl)oxy-4-phenoxyphenyl benzyl ether (3.68 g, 10.6 mmol) and palladium on charcoal (10%, 1.84 g) are taken up in ethyl acetate and subjected to hydrogenation at atmospheric pressure. The reaction is terminated in 15 minutes. The catalyst is removed by filtration and the solvent is evaporated. Purification of the residue by silica-gel flash chromatography gives 2-(2,3-oxopropyl)oxy-4-phenoxyphenol as a colorless solid.

2-(2,3-Oxopropyl)oxy-4-phenoxyphenol (6.0 g, 23 mmol) is taken up in ethanol (250 mL) and treated with aqueous 1N sodium hydroxide (23 mL). The mixture is stirred for 30 minutes, and diluted with ether. The organic phase is washed with 1N hydrochloric acid and water, dried over magnesium sulfate, and evaporated to give 2-hydroxymethyl-6-phenoxy-1,4-benzodioxane as a colorless solid. This is used without further purification.

2-Hydroxymethyl-6-phenoxy-1,4-benzodioxane is converted to 2-(N-hydroxy)aminomethyl-6-phenoxy-1,4-benzodioxane as described in Example 1(a).

EXAMPLE 2 a) 2-[N-(N'-Butylaminocarbonyl)-N-(N''-butylaminocarbonyloxy)]aminomethyl-1,4-benzodioxane (1.24 g, 3.28 mmol) is dissolved in a 1:1 mixture of water/isopropanol and treated with lithium hydroxide monohydrate (1.38 g, 32.8 mmol) for 30 minutes. The mixture is made acidic with 1N hydrochloric acid and diluted with ethyl acetate. The organic layer is washed with saturated aqueous ammonium chloride solution, dried over magnesium sulfate and evaporated. Silica-gel flash chromatography (2:1 hexane/ethyl acetate) gives 2-[N-(N'-butylaminocarbonyl)-N-hydroxy]aminomethyl-1,4-benzodioxane, m.p. 50.0° C., as a colorless solid.

The starting material is prepared as follows:

2-(N-Hydroxy)aminomethyl-1,4-benzodioxane (860 mg, 4.75 mmol) is dissolved in 20 mL of 1,4-dioxane and treated with butyl isocyanate (710 mg, 7.1 mmol). The mixture is heated at reflux for 30 minutes and cooled. The mixture is diluted with ether and washed with saturated aqueous ammonium chloride solution. The organic layer is dried over magnesium sulfate and evaporated to give crude 2-[N-(N'-butylaminocarbonyl)-N-(N''-butylaminocarbonyloxy)]aminomethyl-1,4-dioxane as an oil.

b) Similarly prepared is 2-[N-(N'-benzylaminocarbonyl)-N-hydroxy]aminomethyl-1,4-benzodioxane, m.p. 120° C., as a light tan solid.

c) Similarly prepared is 2-[N-(N'-allylaminocarbonyl)-N-hydroxy]aminomethyl-1,4-benzodioxane as a pale yellow oil.

d) Similarly prepared is 2-[N-(N'-phenylaminocarbonyl)-N-hydroxy]aminomethyl-1,4-benzodioxane.

EXAMPLE 3 a) 2-(N-Hydroxy)aminomethyl-7-phenoxy-1,4-benzodioxane (200 mg, 0.73 mmol) is taken up in acetonitrile (10 mL) and treated with methyl isocyanate (42 mg, 0.73 mmol) at room temperature. This is stirred for 3 hours at room temperature, and diluted with ethyl acetate. The organic phase is washed with saturated aqueous ammonium chloride, dried over magnesium sulfate, and evaporated. Crystallization of the residue from ethyl acetate/hexane gives 2-[N-(N'-methylaminocarbonyl)-N-hydroxy]aminomethyl-7-phenoxy-1,4-benzodioxane, m.p. 60° C., as a glassy solid.

b) Similarly prepared is 2-[N-(N'-methylaminocarbonyl)-N-hydroxy]aminomethyl-6-phenoxy-1,4-benzodioxane, m.p. 150° C., as a colorless solid.

EXAMPLE 4 a) A solution of 2-(N-hydroxy)aminomethyl-6-phenoxy-1,4-benzodioxane (0.67 g) and pyridine (0.49 g, 6.19 mmol) in 30 ml of THF is cooled to 0° C. Acetyl chloride (0.49 g, 6.19 mmol) is slowly added and the mixture is stirred for 45 minutes at 0° C. The mixture is then diluted with ethyl acetate and washed with aqueous 2N HCl, dried (MgSO$_4$) and evaporated to give 2-(N-acetyloxy-N-acetyl)aminomethyl-6-phenoxy-1,4-benzodioxane.

This is dissolved in 40 ml of an isopropanol/water mixture (1:1) and treated with 0.94 g (25 mmol) of lithium hydroxide monohydrate for 20 minutes at room temperature. The mixture is diluted with ether and the organic phase is removed. The aqueous layer is brought to pH of approximately 3 with 2N HCl, and extracted with ether. The combined acidic extracts are dried (MgSO$_4$) and evaporated to dryness to yield 2-(N-hydroxy-N-acetyl)aminomethyl-6-phenoxy-1,4-benzodioxane.

b) Similarly prepared starting with dimethylcarbamoyl chloride is 2-(N-hydroxy-N-dimethylaminocarbonyl)aminomethyl-6-phenoxy-1,4-benzodioxane.

EXAMPLE 5

Similarly to procedures described herein are prepared:

a) 3-(N-aminocarbonyl-N-hydroxy)aminomethyl-6-methoxy-1,4-benzodioxane;

b) 2-(N-acetyl-N-hydroxy)aminomethyl-7-phenoxy-1,4-benzodioxane;

c) 2-(N-aminothiocarbonyl-N-hydroxy)aminomethyl-6-phenoxy-1,4-benzodioxane using trimethylsilyl isothiocyanate instead of trimethylsilyl isocyanate (see Example 1);

d) 2-(N-methylaminocarbonyl-N-hydroxy)aminomethyl-7-(4-fluorophenoxy)-1,4-benzodioxane;

e) 2-(N-aminocarbonyl-N-hydroxy)aminomethylbenzodioxole, starting from benzodioxole-2-carboxylic acid;

f) 3-(N-aminocarbonyl-N-hydroxy)aminomethyl-1,5-benzodioxepin starting from 3-hydroxymethyl-1,5-benzodioxepin.

EXAMPLE 6 a) Preparation of 10,000 tablets each containing 25 mg of the active ingredient, having the formula as follows:

| | |
|---|---|
| 2-(N-aminocarbonyl-N-hydroxy)aminomethyl-7-(4-fluorophenoxy)-1,4-benzodioxane | 250.00 g |
| Lactose | 2,485.00 g |
| Corn starch | 125.00 g |
| Polyethylene glycol 6,000 | 150.00 g |
| Magnesium stearate | 40.00 g |
| Purified water | q.s. |

Procedure: All the powders are passed through a screen with openings of 0.6 mm. The drug substance, lactose, magnesium stearate and half of the starch are mixed in a suitable mixer. The other half of the starch is suspended in 65 ml of water and the suspension added to the boiling solution of the polyethylene glycol in 250 ml of water. The paste formed is added to the powders, which are granulated, if necessary, with an additional amount of water. The granulate is dried overnight at 35° C. broken on a screen with 1.2 mm openings and compressed into tablets, using concave punches uppers bisected.

Analogously tablets are prepared, containing about 10-100 mg of one of the other compounds disclosed and exemplified herein.

b) Preparation of 1,000 capsules each containing 50 mg of the active ingredient, having the formula as follows:

| | |
|---|---|
| 2-(N-aminocarbonyl-N-hydroxy)aminomethyl-7-(4-fluorophenoxy)-1,4-benzodioxane | 50.00 g |
| Lactose | 167.00 g |
| Modified starch | 80.00 g |
| Magnesium stearate | 3.00 g |

Procedure: All the powders are passed through a screen with openings of 0.6 mm. The drug substance is placed in a suitable mixer and mixed first with the magnesium stearate, then with the lactose and starch until homogenous. No. 2 hard gelatin capsules are filled with 300 mg of said mixture each, using a capsule filling machine.

Analogously capsules are prepared, containing about 10-100 mg of the other compounds disclosed and exemplified herein.

What is claimed is:

1. A compound of the formula

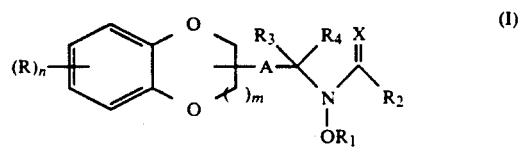

wherein each R independently represents hydrogen, lower alkyl, halogen, trifluoromethyl, lower alkoxy, carbocyclic or heterocyclic aryl, carbocyclic or heterocyclic aryloxy, carbocyclic or heterocyclic aryl-lower alkyloxy, carbocyclic or heterocyclic aryl-lower alkyl, $C_3$–$C_7$-cycloalkyl-lower alkyloxy, or $C_3$–$C_7$-cycloalkyloxy; n represents 1, 2, 3 or 4; m represents 1; A represents a direct bond or lower alkylene; X represents oxygen or sulfur; $R_1$ represents hydrogen, acyl, lower alkoxycarbonyl, aminocarbonyl, mono- or di-lower alkylaminocarbonyl, lower alkenylaminocarbonyl, lower alkynylaminocarbonyl, carbocyclic or heterocyclic aryl-lower alkylaminocarbonyl, carbocyclic or heterocyclic arylaminocarbonyl, $C_3$–$C_7$-cycloalkylaminocarbonyl or $C_3$–$C_7$-cycloalkyl-lower alkylaminocarbonyl; $R_2$ represents lower alkyl, lower alkoxycarbonyl-lower alkyl, $C_3$–$C_7$-cycloalkyl, carbocyclic or heterocyclic aryl, carbocyclic or heterocyclic aryl-lower alkyl, $C_3$–$C_7$-cycloalkyl-lower alkyl, amino, mono- or di-lower alkylamino, lower alkenylamino, lower alkynylamino, carbocyclic or heterocyclic aryl-lower alkylamino, carbocyclic or heterocyclic arylamino, $C_3$–$C_7$-cycloalkylamino, $C_3$–$C_7$-cycloalkyl-lower alkylamino, lower alkoxycarbonyl-lower alkylamino or lower alkoxy; $R_3$ and $R_4$ independently represent hydrogen or lower alkyl; wherein in the above definitions acyl represents lower alkanoyl, benzoyl or benzoyl mono- or di-substituted by one or two radicals selected from lower alkyl, lower alkoxy, halogen, cyano and trifluoromethyl, or 1- or 2-naphthoyl; carbocyclic aryl represents phenyl or phenyl mono- or di-substituted by one or two radicals selected from lower alkyl, lower alkoxy, halogen, cyano and trifluoromethyl, or 1- or 2-naphthyl, and heterocyclic aryl represents pyridyl, quinolyl or thienyl, or any said radical substituted by lower alkyl or halogen; or a pharmaceutically acceptable salt thereof.

2. A compound according to claim 1 wherein A represents a direct bond.

3. A compound according to claim 1 wherein X represents oxygen.

4. A compound according to claim 1 wherein A represents a direct bond and X represents oxygen.

5. A compound according to claim 1 wherein m represents 1; n represents 1 or 2; X represents oxygen; A represents a direct bond; R represents hydrogen, lower alkoxy, halogen, lower alkyl, carbocyclic or heterocyclic aryl-lower alkyloxy or carbocyclic or heterocyclic aryloxy; $R_1$ represents hydrogen or lower alkanoyl; $R_2$ represents lower alkyl, amino, mono- or di-lower alkylamino, or mono-carbocyclic arylamino; $R_3$ and $R_4$ independently represent hydrogen or lower alkyl; or a pharmaceutically acceptable salt thereof.

6. A compound according to claim 1 wherein m and n represent 1; X represents oxygen; A represents a direct bond; R represents hydrogen, lower alkoxy, lower alkyl, carbocyclic aryl-lower alkyloxy or carbocyclic aryloxy; $R_1$ represents hydrogen; $R_2$ represents lower alkyl, amino, mono-or di-lower alkylamino, or monocarbocyclic arylamino; $R_3$ represents hydrogen or lower alkyl; $R_4$ represents hydrogen; or a pharmaceutically acceptable salt thereof.

7. A compound according to claim 1 of formula III

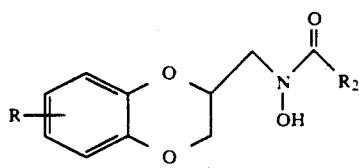

(III)

wherein R represents hydrogen, lower alkyl, carbocyclic aryl, carbocyclic aryl-lower alkyl, lower alkoxy, carbocyclic aryl-lower alkyloxy or carbocyclic aryloxy; and $R_2$ represents mono-lower alkylamino, di-lower alkylamino or amino; or a pharmaceutically acceptable salt thereof.

8. A compound according to claim 1 of formula IV

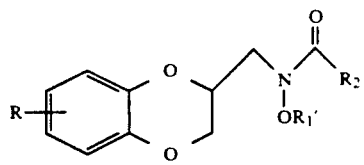

(IV)

wherein R represents hydrogen, lower alkyl, lower alkoxy, carbocyclic aryl-lower alkyloxy, or carbocyclic aryloxy; $R_1'$ represents lower alkanoyl, aminocarbonyl, or mono- or di-lower alkylaminocarbonyl; $R_2$ represents lower alkyl, amino, or mono- or di-lower alkylamino; or a pharmaceutically acceptable salt thereof.

9. A compound according to claim 7 wherein R represents carbocyclic aryloxy.

10. A compound according to claim 7 wherein R represents carbocyclic aryloxy; and $R_2$ represents amino or $C_1$-$C_4$-alkylamino.

11. A compound according to claim 10 wherein carbocyclic aryloxy is attached to the 6 or 7 position of the benzodioxane ring.

12. A compound according to claim 7 being 2-(N-aminocarbonyl-N-hydroxy)-aminomethyl-7-phenoxy-1,4-benzodioxane or a pharmaceutically acceptable salt thereof.

13. A compound according to claim 7 being 2-(N-aminocarbonyl-N-hydroxy)aminomethyl-6-phenoxy-1,4-benzodioxane or a pharmaceutically acceptable salt thereof.

14. A compound according to claim 7 being 2-(N-aminocarbonyl-N-hydroxy)aminomethyl-7-(4-fluorophenoxy)-1,4-benzodioxane or a pharmaceutically acceptable salt thereof.

15. A compound according to claim 7 being 2-[N-(N'-methylaminocarbonyl)-N-hydroxy]aminomethyl-6-phenoxy-1,4-benzodioxane or a pharmaceutically acceptable salt thereof.

16. A pharmaceutical composition suitable for inhibiting 5-lipoxygenase activity in mammals comprising an effective 5-lipoxygenase inhibiting amount of a compound of claim 1 in combination with one or more pharmaceutically acceptable carriers.

17. A method of inhibiting 5-lipoxygenase activity and of treating disorders in mammals which are responsive to such inhibition which comprises administering to a mammal in need thereof an effective 5-lipoxygenase inhibiting amount of a compound of claim 1 or of a said compound in combination with one or more pharmaceutically acceptable carriers.

18. A method according to claim 17 of treating allergic, inflammatory, cardiovascular, pulmonary, arthritic, and cutaneous disorders responsive to inhibition of 5-lipoxygenase activity.

* * * * *